US009040919B2

(12) United States Patent　(10) Patent No.: US 9,040,919 B2
Darcie et al.　(45) Date of Patent: May 26, 2015

(54) PHOTOMIXER-WAVEGUIDE COUPLING TAPERS

(76) Inventors: Thomas E. Darcie, Victoria (CA); Hamid Pahlevaninezhad, Victoria (CA)

( * ) Notice: Subject to any disclaimer, the term of this patent is extended or adjusted under 35 U.S.C. 154(b) by 664 days.

(21) Appl. No.: 13/281,064

(22) Filed: Oct. 25, 2011

(65) Prior Publication Data

US 2012/0097850 A1　Apr. 26, 2012

Related U.S. Application Data

(60) Provisional application No. 61/406,535, filed on Oct. 25, 2010.

(51) Int. Cl.

| G01N 21/35 | (2014.01) |
|---|---|
| G02B 6/10 | (2006.01) |
| G01J 3/02 | (2006.01) |
| G01J 3/42 | (2006.01) |
| G01N 21/3581 | (2014.01) |
| G02B 6/122 | (2006.01) |
| G01N 21/3504 | (2014.01) |
| G01N 21/3563 | (2014.01) |
| G01N 21/3577 | (2014.01) |

(52) U.S. Cl.
CPC ............... *G02B 6/102* (2013.01); *G01J 3/0205* (2013.01); *G01J 3/42* (2013.01); *G01N 21/3581* (2013.01); *G02B 6/1228* (2013.01); *G01N 21/3504* (2013.01); *G01N 21/3563* (2013.01); *G01N 21/3577* (2013.01)

(58) Field of Classification Search
CPC ........ G02B 6/14; G02B 6/382; G02B 6/3822; G01N 21/3586
USPC .......... 250/340, 504 R, 349, 353; 385/43, 50, 385/27, 28
See application file for complete search history.

(56) References Cited

U.S. PATENT DOCUMENTS

| 5,009,475 | A | * | 4/1991 | Knudson ....................... 385/116 |
|---|---|---|---|---|
| 5,199,092 | A | * | 3/1993 | Stegmueller ..................... 385/50 |
| 5,265,177 | A | * | 11/1993 | Cho et al. ........................ 385/14 |
| 5,854,868 | A | * | 12/1998 | Yoshimura et al. ............. 385/50 |
| 6,100,853 | A | * | 8/2000 | Schaffner et al. ............. 343/771 |
| 6,253,015 | B1 | * | 6/2001 | Ukrainczyk ................... 385/130 |
| 6,268,781 | B1 | * | 7/2001 | Schaffner ........................ 333/26 |
| 6,282,345 | B1 | * | 8/2001 | Schimpe ......................... 385/50 |
| 6,353,416 | B1 | * | 3/2002 | Hopkins et al. .............. 343/767 |
| 6,476,596 | B1 | * | 11/2002 | Wraback et al. ........... 250/338.4 |
| 7,068,870 | B2 | * | 6/2006 | Steinberg et al. ............... 385/14 |
| 7,103,245 | B2 | * | 9/2006 | Lee et al. ........................ 385/28 |
| 7,612,733 | B2 | * | 11/2009 | Weiss et al. ................... 343/860 |
| 7,851,782 | B2 | * | 12/2010 | Seeds et al. ..................... 257/21 |
| 8,031,991 | B2 | * | 10/2011 | Webster et al. ................. 385/28 |

(Continued)

*Primary Examiner* — David Porta
*Assistant Examiner* — Djura Malevic
(74) *Attorney, Agent, or Firm* — Klarquist Sparkman, LLP

(57) ABSTRACT

Disclosed are systems and methods for improving the performance of systems for generating and detecting electromagnetic radiation at terahertz (THz) frequencies. Embodiments of the systems and methods include the fabrication and use of coupling tapers to provide efficient transfer of THz radiation between a photomixer and a waveguide that supports a propagating THz mode. A representative system comprises of a photomixer to convert high-frequency components of an optical pump signal into corresponding electrical THz frequencies, a waveguide that supports a propagating THz mode, and a matching taper that effectively converts the highly localized currents generated by the photomixer to the mode supported by the waveguide.

26 Claims, 5 Drawing Sheets

(56) References Cited

U.S. PATENT DOCUMENTS

| | | | |
|---|---|---|---|
| 8,045,832 B2 * | 10/2011 | Pan et al. | 385/43 |
| 8,116,602 B2 * | 2/2012 | Little et al. | 385/27 |
| 8,309,925 B2 * | 11/2012 | Mendis et al. | 250/336.1 |
| 8,498,539 B1 * | 7/2013 | Ilchenko et al. | 398/115 |
| 8,542,965 B2 * | 9/2013 | Deliwala | 385/43 |
| 2002/0031296 A1 * | 3/2002 | Lee et al. | 385/28 |
| 2003/0012493 A1 * | 1/2003 | Lee et al. | 385/28 |
| 2003/0198269 A1 * | 10/2003 | Wesstrom | 372/50 |
| 2004/0017976 A1 * | 1/2004 | Luo et al. | 385/43 |
| 2004/0037497 A1 * | 2/2004 | Lee | 385/28 |
| 2004/0057667 A1 * | 3/2004 | Yamada et al. | 385/43 |
| 2004/0114868 A1 * | 6/2004 | Roberson | 385/43 |
| 2004/0114869 A1 * | 6/2004 | Fike et al. | 385/43 |
| 2004/0264863 A1 * | 12/2004 | Suzuki et al. | 385/43 |
| 2004/0264903 A1 * | 12/2004 | Dridi et al. | 385/129 |
| 2005/0258368 A1 * | 11/2005 | Ohtake et al. | 250/338.1 |
| 2006/0204175 A1 * | 9/2006 | Laurent-Lund et al. | 385/43 |
| 2006/0214114 A1 * | 9/2006 | Liu et al. | 250/474.1 |
| 2006/0228074 A1 * | 10/2006 | Lipson et al. | 385/42 |
| 2007/0090089 A1 * | 4/2007 | Chang et al. | 216/41 |
| 2008/0002928 A1 * | 1/2008 | Li | 385/14 |
| 2008/0023633 A1 * | 1/2008 | Mittleman et al. | 250/341.1 |
| 2008/0152279 A1 * | 6/2008 | Feng et al. | 385/28 |
| 2008/0217538 A1 * | 9/2008 | Ouchi et al. | 250/338.4 |
| 2008/0224931 A1 * | 9/2008 | Weiss et al. | 343/700 MS |
| 2008/0265165 A1 * | 10/2008 | Yeh et al. | 250/341.1 |
| 2008/0309577 A1 * | 12/2008 | Mittleman et al. | 343/850 |
| 2010/0054296 A1 * | 3/2010 | Ohtake et al. | 372/80 |
| 2010/0073110 A1 * | 3/2010 | Nathan et al. | 333/218 |
| 2010/0084570 A1 * | 4/2010 | Katagiri | 250/458.1 |
| 2010/0172619 A1 * | 7/2010 | Li | 385/129 |
| 2010/0187402 A1 * | 7/2010 | Hochberg et al. | 250/208.1 |
| 2010/0187442 A1 * | 7/2010 | Hochberg et al. | 250/492.1 |
| 2011/0206323 A1 * | 8/2011 | Zhang et al. | 385/50 |
| 2012/0032081 A1 * | 2/2012 | Itsuji | 250/340 |
| 2012/0194901 A1 * | 8/2012 | Bravo-Abad et al. | 359/330 |

* cited by examiner

PHOTOMIXER-WAVEGUIDE COUPLING TAPERS

CROSS REFERENCE TO RELATED APPLICATION

This application claims the benefit of U.S. Provisional Application 61/406,535, filed Oct. 25, 2010, which is incorporated herein by reference.

FIELD

The invention relates to generation, transmission, and detection of signals at THz frequencies with applications in spectroscopy, biomedical analysis, analysis of substances and materials, and communications.

BACKGROUND AND SUMMARY

Terahertz (THz) systems have become important for a wide variety of applications in analysis, diagnostics, and potentially communications. A large number of significant technical innovations over the last decade has made the terahertz frequency range (0.1 to 10 THz) increasingly accessible for applications in science and industry. However, difficulty in generating, manipulating, and detecting terahertz radiation continues to plague most applications. Source powers (from sources that are readily attainable) tend to be low. Focusing optics is costly, difficult to align, and has high loss. Detectors are expensive, inefficient (particularly at high frequencies), and usually require alignment with an optical pump source. In combination, these factors restrict terahertz applications to exploratory and scientific investigation, rather than to what could become large markets and relatively high-volume applications.

One of the most common applications for THz technology is spectroscopy. In spectroscopy, the frequency dependence of transmission of electromagnetic radiation through a sample reveals a unique fingerprint of substances being studied. In the THz frequency range, this fingerprint results from unique rotational and vibrational energy states associated with complex molecules, providing information related to composition and conformal state. While other approaches (e.g. Raman spectroscopy) offer views into molecular form and function, THz spectroscopy provides a unique and complementary view. As a result, an easy to use and cost-effective THz spectrometer will stimulate environmental, medical, material science, and other applications.

Both time-domain spectrometers (TDS) and frequency-domain spectrometers (FDS) are well established. At the heart of each, as shown by the dotted lines in FIG. 1, is a THz generation-analysis-detection (TGAD) module 100. In a typical TDS, a short laser pulse (50 fsec) is split and focused on separate transmit and receive photomixers (PM) 110. The terms photomixer and photoconductive switch are generally used in reference to FDS and TDS operation, respectively. As used herein, the term photomixer is applicable to both modes of operation. The transmit PM is biased such that the change in conductivity induced by absorption of the short laser pulse creates a current pulse that drives a small dipole antenna, radiating THz frequencies that are captured by a silicon lens 120 to produce the diverging THz beam shown 130. A TEFLON polytetrafluoroethylene lens 140 then creates a collimated THz beam 150 that is used to probe the sample. After passing through a sample, the THz beam 150 is focused to the receive PM 110 where it is sampled by the short laser pulse to produce a small current as measured typically with a lock-in-amplifier. The sampling time is adjusted using a variable optical delay, in this case introduced by varying a retroreflector. FDS operate in the same manner except that instead of using a short laser pulse, two continuous-wave lasers separated in optical frequency by the THz frequency are combined to produce the THz pump intensity variations.

Many applications for THz analysis have been defined [1], including measurement of gas-phase samples, liquids and solids. Examples include:

Breath analysis: Non-invasive diagnostics of disease: Detecting volatile compounds in breath has gained considerable attention for medical diagnosis [2] due to its non-invasive nature and the potential for breath-by-breath analysis. Numerous compounds in exhaled breath are valuable indicators of an individual's health status [3]. The Federal Drug Administration (FDA) has approved some compounds for breath testing, including ethanol ($C_2H_5OH$) for law enforcement, hydrogen for carbohydrate metabolism, nitric oxide (NO) for asthma, carbon monoxide (CO) for neonate jaundice, $^{13}CO_2$ for $H.\ pylori$ infection (related to stomach cancer and normally asymptomatic), and branched hydrocarbons for heart transplant rejection. Additionally, increased breath ammonia ($NH_3$) is found to relate to kidney and liver dysfunction, breath acetone is higher in diabetes, and the level of aldehydes such as methanol ($CH_2O$) can be used to screen lung and breast cancers. Currently applied analytical instruments include mass and mid-IR spectrometers. Although these are large and expensive, both are in widespread use, supporting diverse instrumentation and diagnostic industries. THz spectrometers can record fast processes, opening up a unique potential for real-time analysis of exhaled air.

Security: Several applications exist in the area of explosive detection, where flames, plumes, and explosive vapour are of great interest. Collective motions in molecules found in common explosives correspond to features in THz spectra that can be used for unique identification. There have been extensive studies on the THz spectroscopy of explosives like DNT, RDX, HMX, TNT, and PETN [4]. Also, understanding combustion requires knowing the species present and the spatial distribution in the flame, as measured using THz in [5].

Environmental: Rotational transitions of light polar molecules and low-frequency vibrational modes of large molecular systems can be probed by THz spectroscopy, opening applications in sensing atmospheric pollutants and detecting airborne chemicals. Atmospheric pollutants like hydrogen sulphide (H2S), OCS, formaldehyde (H2CO), and ammonia (NH3) possess intense THz transitions [6]. Volatile organic compounds (VOCs) are of high interest in manufacturing and oil and gas industries, and are potentially detectable in real time using the proposed instrument.

Scientific: Large numbers of applications have been considered within the laboratory, including studying the absorption and dispersion of compounds [7], dynamics of laser induced plasmas [8], real-time trace gas detection [9], and the analysis of chemical compositions [10].

THz generation-analysis-detection (TGAD) modules used in existing THz spectrometers (FIG. 1) use discrete optical components to form free-space THz beams. These suffer from mechanical, performance, and cost challenges. Mechanically, they are bulky, require difficult alignment and are subject to mechanical instability. Several factors limit performance. Significant restrictions are placed on the diameter and length of the interaction region and on the achievable electric field strength within this interaction region. Given the size and the need for adjustment, it is difficult to isolate measurements from external factors, such as water vapour that must be removed by purging with dry gas. Most importantly, numerous elements in cascade introduce substantial loss, including frequency dependence of the antennas, reducing dynamic range and bandwidth. Several factors combine leading to high cost, led by the required optical (both THz and pump laser) components and alignment. Hence there is a compelling need to improve upon the state of the art.

Confining THz radiation within waveguide structures offers tremendous advantages in size, performance, and versatility, driving research on many types of THz waveguides, such as coplanar strip lines [11], metal pipes [12], dielectric fibers [13], etc. The single-wire waveguide [14] shows low loss and low dispersion, but it is difficult to couple the output from a typical PM to the radially-polarized mode supported by this waveguide.

Two-wire waveguides [15,16] combine both low loss and efficient coupling properties. The mode supported by this type of waveguide is very similar to the field emitted from a simple dipole. For the TEM mode there is no cutoff frequency and no dispersion. Confining electromagnetic energy in a small area between the two wires is another important advantage, making it more practical and more tolerant to bend loss [17].

For low-loss transmission over the terahertz band, the two-wire waveguide described above has a mode area of typically 20 mm$^2$. For THz operation, active components like photomixers have very small active areas (e.g. 20 µm$^2$)—much smaller than the mode area of the low-loss passive structures described above. Also, unlike the passive components described above, active components are fabricated in-plane, typically on III-V semiconductors. Therefore, some technique for matching these very small active devices to these much larger waveguide structures is required.

Disclosed herein are methods and apparatus that permit efficient transitions from small and active components like a photomixer to a larger waveguide structure. It is anticipated that such transitions will be essential in making THz measurement affordable and easy to use, improving performance, simplifying alignment and adding mechanical stability. In addition, the novel methods disclosed for coupling between THz sources and THz waveguides will have broad application in other areas, such as communications.

In some examples, systems for transmission of terahertz signals comprise at least one terahertz device configured produce a terahertz electrical signal, and a terahertz waveguide operable at terahertz frequencies configured to transport the terahertz electrical signal. A mode-matching taper is situated so as to couple the terahertz device to the terahertz waveguide and direct the terahertz electrical signal from the terahertz device to the terahertz waveguide. In some embodiments, the mode-matching taper comprises a substrate and a first tapered waveguide section situated on the substrate so as to substantially match a component of a propagating electrical mode associated with the terahertz electrical signal produced by the terahertz device. In further examples, the mode-matching taper further comprises a second tapered waveguide section situated on the substrate so as to substantially match a component of a mode supported by the terahertz device to a mode associated with the terahertz waveguide. In some examples, the substrate comprises a planar surface and the first and second waveguide sections are situated on the planar surface. In representative embodiments, the first waveguide section is defined by at least one conductor situated on the planar surface of the substrate and includes an in-plane taper at the planar surface so that the first waveguide section is associated with a waveguide mode that substantially matches an in-plane component of the electrical mode associated with the terahertz electrical signal, and the second waveguide section includes a taper normal to the plane of the surface so as to substantially match the component of the electrical signal produced by the terahertz device normal to the planar substrate and a mode associated with the terahertz waveguide. In other representative examples, a cap layer is situated on the planar surface, and the substrate and the cap layer are at least one of silicon, GaAs, or InGaAs. In other embodiments, the substrate includes a thinned portion situated along at least a portion of the mode-matching taper or substrate is a one-dimensional photonic crystal. In one embodiment, the terahertz waveguide is a two wire waveguide. In other examples, the mode-matching taper includes at least one tapered section corresponding to a tapered slotline, a tapered coplanar stripline, a tapered microstrip, a tapered stripline, or a tapered coplanar waveguide. In some embodiments, the mode-matching taper includes a first section defined by a tapered slotline having a taper in a first direction and a second section defined by at least two tapered wires, wherein each of the two wires is tapered in a second direction that is perpendicular to the first direction.

According to other examples, mode-matching tapers for coupling between a terahertz device and a terahertz waveguide include a device port configured to couple to a terahertz device and a waveguide port configured to couple to the terahertz waveguide. A tapered waveguide is situated so as to connect the device port and the waveguide port, wherein a dimension of the tapered waveguide transitions from a dimension associated with the device port to a dimension associated with the waveguide port. In other examples, the tapered waveguide includes a plurality of steps or continuously so as to transition from the dimension associated with the device port to the dimension associated with the waveguide port. In some examples, the waveguide port is configured to couple to a two wire transmission line. According to other examples, the tapered waveguide is defined on a substrate and a terahertz device is formed at least partially in the substrate. In additional examples, a cap layer is situated on the substrate and configured to suppress terahertz wave coupling into the substrate based on a thinned region of the substrate situated at the tapered waveguide, or with a substrate that is a one-dimensional photonic crystal.

Representative methods include transmitting a terahertz electrical signal with a terahertz waveguide and coupling the terahertz electrical signal to terahertz device with a mode-matching taper situated between the terahertz waveguide and the terahertz device. In some examples, the terahertz device is a terahertz generator or a terahertz detector. In other examples, the terahertz electrical signal is directed from the terahertz waveguide to a specimen, and the terahertz electrical signal is detected after interaction with the specimen. In further embodiments, the terahertz electrical signal is generated with a pulsed optical beam or based on a combination of two or more optical beams having a terahertz frequency difference.

These and other features and aspects of the disclosed technology are described in further detail below with reference to the accompanying drawings.

BRIEF DESCRIPTION OF THE DRAWINGS

FIG. 5(a) illustrates a taper structure configured to couple a THz wave into a two-wire waveguide at 1 THz, and FIG. 5(b) illustrates shock wave radiation in the slot-line on a silicon substrate.

DETAILED DESCRIPTION

As used in this application and in the claims, the singular form's "a," "an," and "the" include the plural forms unless the context clearly dictates otherwise. Additionally, the term "includes" means "comprises." Further, the term "coupled" does not exclude the presence of intermediate elements between the coupled items. The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

In what follows, the term photomixer refers to any photoconductive or other photoresponsive material configured to receive either a pulsed or continuous wave optical input (typically from a pulsed or continuous wave laser source) to generate currents with terahertz frequency components. The term terahertz frequency band refers to the region of the electromagnetic spectrum ranging between 100 GHz and 10 THz. The term active terahertz device refers to any photomixer, photodetector, electronic diode or transistor or collection of such devices into integrated circuits operable to generate or detect electromagnetic radiation at terahertz frequencies. Such active terahertz devices are also referred to herein as terahertz devices, terahertz generators, or terahertz detectors. The term terahertz waveguide refers to any guided wave structure, including but not limited to two wire waveguides, rectangular metal waveguides, and dielectric waveguides operable to transmit terahertz electromagnetic radiation. The term mode-matching taper is used to describe the gradual transition from one mode size and shape to another. Mode-matching tapers can be based on slotlines, coplanar striplines, microstrips, striplines, coplanar waveguides, or other waveguides. The term radiation loss suppression mechanism refers to mechanisms by which shock-wave radiation loss is prevented, including but not limited to the addition of a symmetric cap layer, thinning of the substrate under the waveguide, and the incorporation of a periodic layered structure.

Figure 1:
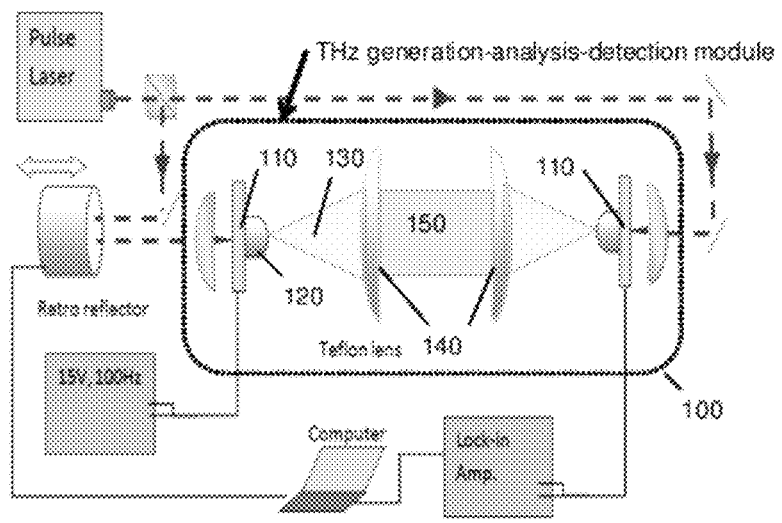
FIG. 1 illustrates a typical configuration for a prior art time-domain THz spectrometer.
Figure 2:
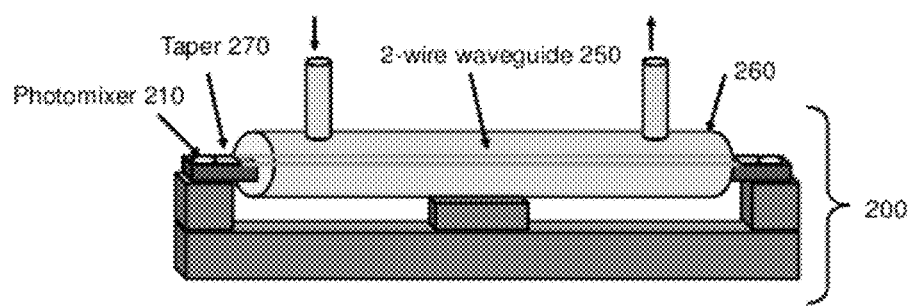
FIG. 2 illustrates a new terahertz generation-analysis-detection (TGAD) module based on transmit and receive photomixers (PMs) coupled through tapers to a 2-wire waveguide.

A conventional TGAD module 100 as shown in FIG. 1 can be replaced with an illustrative example of an embodiment of the disclosed technology. The representative improved module uses a two-wire waveguide and novel PM-waveguide coupling tapers, shown in FIG. 2, to produce a small high-performance THz spectrometer. In one preferred embodiment, a TGAD module 200 consists of a compact 2-wire (gold) waveguide 250 supported within a small glass sample tube 260 and driven by fiber-coupled PMs 210. The typically 10 cm long and 300 µM diameter gold wires are separated by roughly 1 mm and supported within the glass tube by stretching with modest tension between two plastic end caps. Gas ports allow purge gas and the admission of gas samples. Novel aspects include the design of the waveguide 250 and the coupling from PMs into and out of the waveguide via novel tapers 270.

Figure 3:
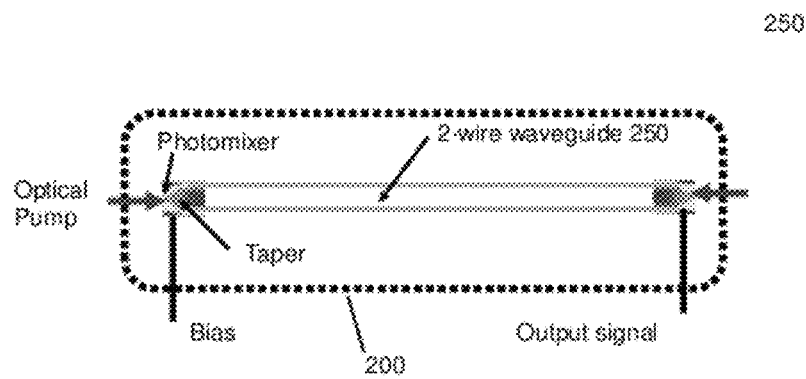
FIG. 3 is an alternative view of a terahertz generation-analysis-detection (TGAD) module based on transmit and receive PMs coupled through tapers to a 2-wire waveguide.
Figure 5:
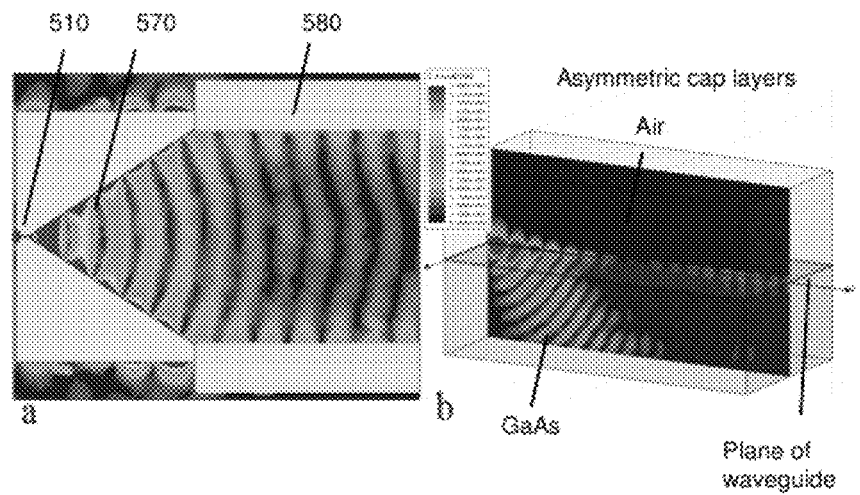
FIG. 5 illustrates coupling from PM and 2-wire waveguide by tapered gold slot structure.

FIG. 3 shows an alternative view of TGAD module 200, showing tapers and PMs 210 and tapers 270 integrated onto the same chip, as discussed in more detail below with regard to FIG. 5. Module 200 can be substituted for module 100 in FIG. 1. A variety of methods can be devised to place liquid or solid samples within the gap between the gold wires. This configuration also presumes that a PM is used as a detector, as is well known in the prior art. Alternatively, the PM-taper device can be used only at one end. For example, the waveguide may alternatively be terminated on another type of detector like a Golay cell. Also, as might be encountered in a circuit operating at THz frequencies, active (e.g. mixer, transistor) or passive (e.g., antenna, matching stub) components might be connected between the waveguide conductors.

It should also be noted that the discussion so far has concentrated on photomixers, or equivalently photoconductors, that convert modulated optical intensity into a change in conductance. Embodiments of the inventions disclosed herein would also be applicable if the source of the high-frequency electrical signals were high-speed photodetectors, which convert to modulated optical intensity directly into photocurrent with high-frequency components, or any form of an active electronic circuit using, for example, very high speed diodes or transistors to form an oscillator, frequency multiplier, mixer, or other terahertz device. As will be obvious to one skilled in the art, significant advantage may be achieved in coupling any of these components to low loss terahertz waveguides.

Figure 4:
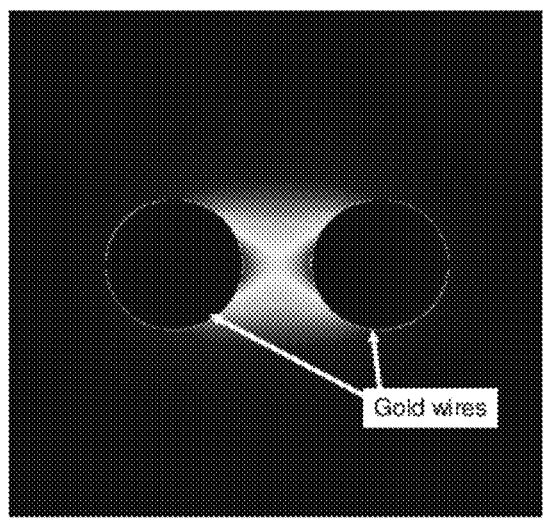
FIG. 4 is a cross sectioned view of E-field for a 2-wire waveguide showing strong concentration of energy between wires with 500 µm radii and 1.5 mm center-to-center wire spacing.

FIG. 4 shows the electric field distribution of the TEM mode of the two-wire waveguide. It must be understood that a variety of waveguide structures could be contemplated within the scope of the present invention and that this two-wire waveguide is merely representative. The field distribution is highly dependent on the radii of the wires and the separation distance. Designs can be based on a detailed understanding [16] of the field distribution and loss as a function of physical dimensions. Waveguide loss over a 10 cm length may be a small fraction of a dB.

Direct coupling from PMs or photodetectors to the waveguide is based on novel tapers. (In conventional systems, PMs are coupled to antennas.) The first stage of this taper (FIG. 5a) expands the field to two parallel gold strips, or a slot waveguide, all fabricated on the planar PM substrate. The terahertz current, generated at the small gap in the active area 510, excites the TEM mode of a slot-line; the separation of the plates becomes gradually wider in the form of a taper 570 to expand the field to the size comparable to the waveguide's 580 dimensions. It should also be understood that this particular implementation of the taper is just one example, and that other means of expanding the field size may be contemplated, depending on the form of the waveguides used.

The second stage converts from the planar strips 580 to lower-loss round gold wires that have been tapered to flat for attachment to the chip, or to whatever form of waveguide is used. One skilled in the art will recognize that a variety of similar tapers can be contemplated to connect to a variety of waveguide structures.

Figure 6:
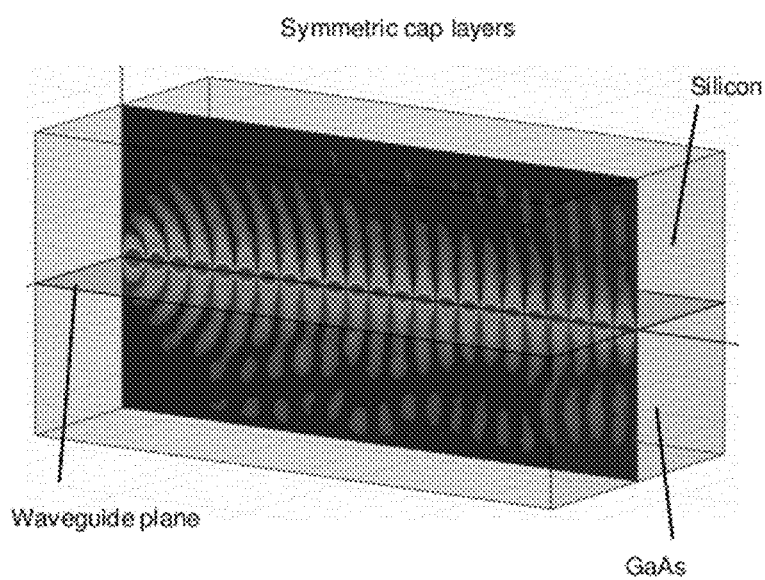
FIG. 6 depicts simulation results for the slot-line on a silicon substrate with silicon cap on top and 10 µm gap.

Fabricating waveguides on the surface of a high dielectric substrate such as GaAs requires careful consideration. The high velocity mismatch between fields propagating above the substrate and below does not allow the TEM mode to propagate, and simulations presented in FIG. 5b show that the electric field is drawn into the substrate and lost. This loss mechanism has been referred to as shock wave radiation loss. To prevent this, a variety of techniques may be employed. Since the photomixers are typically fabricated on GaAs or similar alloys, a matching upper GaAs, silicon, or other cap layer can be used to compensate for this velocity mismatch. The efficacy of this approach can be seen in FIG. 6, which shows a simulated mode propagating with low loss through such a structure.

Figure 7:
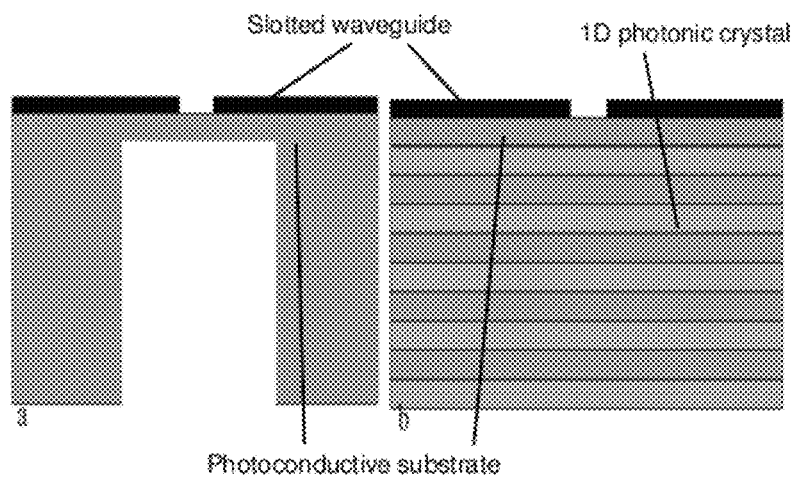
FIG. 7 (a) includes a schematic diagram of a slot-line with 10 µm gap on a silicon substrate thinned beneath the gap, and (b) slot-line on a layered substrate (alternating layers of Si and $SiO_2$ with 15 µm and 40 µm thicknesses, respectively).

Another possible solution for the mismatch problem is to make the thickness of the substrate right below the slot, small compared to the wavelength (less than typically 10 μm for GaAs) so that the shock waves cannot be excited as shown in FIG. 7(a).

Figure 8:
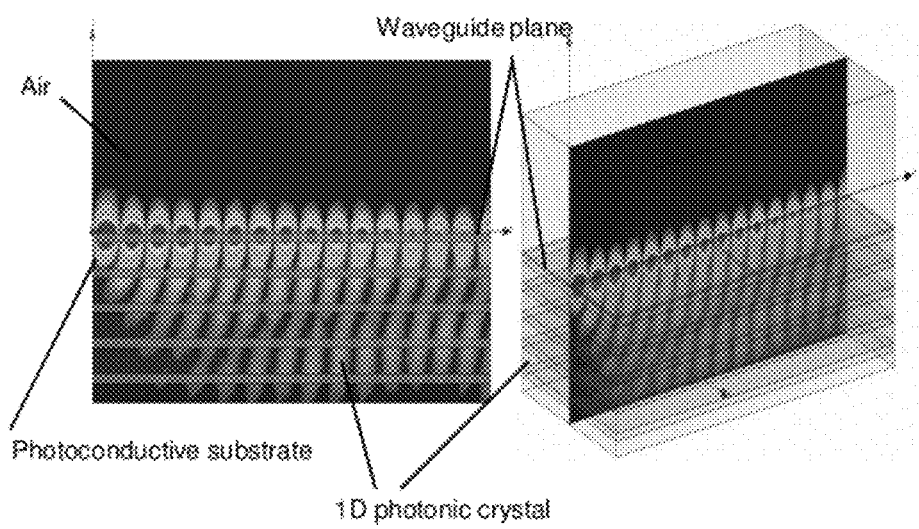
FIG. 8 illustrates numerical simulation results for the layered substrate at 1 THz.

Yet another solution, as shown in FIG. 7b, is to use a layered substrate to avoid propagation of the terahertz wave into the substrate. The layered substrate is a 1-dimensional photonic crystal that creates a band-gap to avoid propagation of waves into the substrate for a certain range of frequency. It can be shown that surface waves can be supported by the layered substrate with exponentially decaying field amplitude in air and the substrate for the appropriate thicknesses of the layers. Therefore, we confine the waves in one dimension by the metal plates and in the other by the layered substrate. FIG. 8 shows how the layered structure confines most of the electromagnetic energy at the surface.

Figure 9:
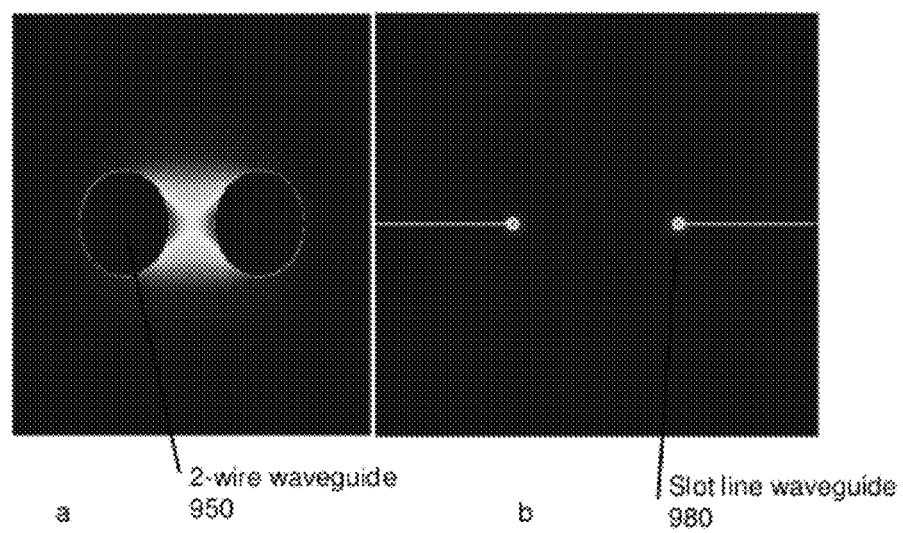
FIG. 9 illustrates field distribution of the TEM mode for (a) a two-wire waveguide with 500 µm radii and 1.5 mm center-to-center wire spacing, (b) and the slot-line with 500 µm gap.

The second stage of the taper is used since the field distribution of the TEM modes supported by the slot-line 980 and the two-wire waveguide 950 are rather different, as shown in FIG. 9. In the slot-line the field is mostly concentrated on the edges of the plates while it is more distributed on the surfaces of the wires for the two-wire waveguide. A two-wire waveguide with the wires squeezed to rectangular shapes at the input port of the waveguide can be used. This way, the field distribution changes gradually from the slot-line field distribution to the TEM mode supported by the two-wire waveguide.

The disclosed TGAD modules based on waveguides and tapers offer advantages in mechanical design, performance, and cost. Mechanically, the device is compact, requires no alignment, and is easier to isolate from environmental variability, including humidity and vibration. Advantages in performance include reduced THz loss, which translates to higher dynamic range, and potentially very long interaction lengths, an important factor for trace gas-phase measurements. A major advantage is that the frequency response is no longer constrained by the resonant response of the antennas. Finally, since the THz signal is coupled from the edge of the PM chip, the receiver is more easily isolated from laser-induced thermal interference from the transmitter. As for cost, the parts for the THz waveguide assembly cost a small fraction of the cost of typical bulk optic components. Optical pump coupling is normal to the chip surface, facilitating easier attachment of optical fibers. Operational cost is reduced as alignment is not needed and need for mechanical isolation is reduced.

In view of the many possible embodiments to which the disclosed principles of invention may be applied, it should be recognized that the illustrated embodiments are only preferred examples and should not be taken as limiting in scope. We claim all that is encompassed by the pending claims.

REFERENCES

The disclosed technology is described above with reference to the following documents, all of which are incorporated herein by reference.

1. H. H. Mantsch, D. Naumann, "Terahertz spectroscopy: The renaissance of far infrared spectroscopy", Journal of Molecular Structure 964, 1-4, 2010.
2. A. Amann, P. Spanel, D. Smith, "Breath analysis: The approach towards clinical applications", Mini-Reviews in Medical Chemistry, 7, 115-129, 2007.
3. A. Manolis, "The diagnostic potential of breath analysis", Clinic Chemistry, Vol. 29, No. 1, 5-15, 1983.
4. M. R. Leahy-Hoppa, M. J. Fitch, R. Osiander, "Terahertz spectroscopy techniques for explosives detection", Springer, Analytical and Bioanalytical Chemistry, Vol. 395, No. 2, 247-257, 2009.
5. R. A. Cheville, D. Grischkowsky, "Far-field terahertz time-domain spectroscopy of flames", Opt. Lett., 20, 15, 1995.
6. F. Hindle, A. Cuisset, R. Bocquet, G. Mouret, "Continuous-wave terahertz by photomixing: applications to gas phase pollutant detection and quantification", Elsevier, C. R. Physique 9, 262-275, 2008.
7. D. Grischkowsky, S. Keiding, M. van Exter, C. Fattinger, "Far-infrared time-domain spectroscopy with terahertz beams of dielectrics and semiconductors", Journal of OSA B, Vol. 7, No. 10, 1990.
8. J. Liu, X. C. Zhang, "Plasma characterization using terahertz-wave-enhanced fluorescence", Applied Physics Letters 96, 041505, 2010.
9. S. A. Harmon, A. R. Cheville, "Part-per million gas detection from long-baseline THz spectroscopy", Applied Physics Letters, Vol. 85, No. 11, 2004.
10. Y. Watanabe, et al, "Component analysis of chemical mixtures using terahertz spectroscopic imaging", Elsevier, Optics Communications 234, 125-129, 2004.
11. M. Y. Frankel, S. Gupta, J. A. Valdmanis, G. A. Mourou, "Terahertz attenuation and dispersion characteristics of coplanar transmission lines," IEEE Transaction on Microwave Theory and Techniques 39, 910-916, (1991).
12. C G. Gallot, S. P. Jamison, R. W. McGowan, D. Grischkowsky, "Terahertz waveguides," J. Opt. Soc. Am. B 17, 851-863 (2000).
13. S. P. Jamison, R. W. McGowan, D. Grischkowsky, "Single-mode waveguide propagation and reshaping of sub-ps terahertz pulses in sapphire fibers," Appl. Phys. Lett. 76, 1987-1989 (2000).
14. K. Wang, D. Mittleman, "Metal wires for terahertz wave guiding," Nature 432, 376-379 (2004).
15. M. K. Mbonye, V. Astley, W. L. Chan, J. A. Deibel, D. M. Mittleman, "A terahertz dual wire waveguide," in *Lasers and Electro-Optics Conference*, Optical Society of America, 2007, paper CThLL1.
16. H. Pahlevaninezhad, T. E. Darcie, B. Heshmat, "Two-wire waveguide for terahertz," Opt. Express 18, 7415-7420 (2010).

17. M. K. Mbonye, R. Mendis, D. M. Mittleman, "A terahertz two-wire waveguide with low bending loss," Appl. Phys. Lett. 95, 233506 (2009).

18. V. Pacebutas et al Appl. Phys. Lett. 97, 031111 (2010).

We claim:

1. A system for transmission of terahertz signals comprising:
    at least one terahertz device configured produce a terahertz electrical signal;
    a terahertz waveguide operable at terahertz frequencies configured to transport the terahertz electrical signal, the terahertz waveguide defined by at least one conductor; and
    a conductive mode-matching taper situated so as to couple the terahertz device to the terahertz waveguide so as to direct the terahertz electrical signal from the terahertz device to the terahertz waveguide.

2. The system of claim 1, wherein the mode-matching taper comprises:
    a substrate; and
    a first tapered waveguide section situated on the substrate so as to substantially match a component of a propagating electrical mode associated with the terahertz electrical signal produced by the terahertz device.

3. The system of claim 2, wherein the mode-matching taper further comprises a second tapered waveguide section situated on the substrate so as to substantially match a component of a mode supported by the terahertz device to a mode associated with the terahertz waveguide.

4. The system of claim 3, wherein the substrate comprises a planar surface and the first and second waveguide sections are situated on the planar surface.

5. The system of claim 4, wherein the first waveguide section is defined by at least one conductor situated on the planar surface of the substrate and includes an in-plane taper at the planar surface so that the first waveguide section is associated with a waveguide mode that substantially matches an in-plane component of the electrical mode associated with the terahertz electrical signal.

6. The system of claim 5, wherein the second waveguide section includes a taper normal to the plane of the surface so as to substantially match the component of the electrical signal produced by the terahertz device normal to the planar substrate and a mode associated with the terahertz waveguide.

7. The system of claim 4, further comprising a cap layer situated on the planar surface.

8. The system of claim 7, wherein the substrate and the cap layer are at least one of silicon, GaAs, or InGaAs.

9. The system of claim 4, wherein the substrate includes a thinned portion situated along at least a portion of the mode-matching taper.

10. The system of claim 4, wherein the substrate is a one-dimensional terahertz photonic crystal.

11. The system of claim 8, wherein the terahertz device is at least partially defined in the substrate.

12. The system of claim 1, wherein the terahertz waveguide is a two wire waveguide.

13. The system of claim 1, wherein the mode-matching taper includes at least one tapered section corresponding to a tapered slotline, a tapered coplanar stripline, or a tapered coplanar waveguide.

14. The system of claim 1, wherein the mode-matching taper includes a first section defined by a tapered slotline having a taper in a first direction and a second section defined by at least two tapered wires, wherein each of the two wires is tapered in a second direction that is perpendicular to the first direction.

15. The system of claim 1, wherein the terahertz device is a photomixer or a photoconductor and is configured to produce the terahertz electrical signal in response to at least one received optical signal.

16. A mode-matching taper, for coupling between a terahertz device and a terahertz waveguide, comprising:
    a device port configured to couple to a terahertz device;
    a waveguide port configured to couple to the terahertz waveguide;
    a tapered metallic waveguide connecting the device port and the waveguide port, wherein a dimension of the tapered metallic waveguide transitions from a dimension associated with the device port to a dimension associated with the waveguide port.

17. The taper of claim 16, where the tapered metallic waveguide includes a plurality of steps so as to transition from the dimension associated with the device port to the dimension associated with the waveguide port.

18. The taper of claim 16, where the tapered metallic waveguide transitions substantially continuously from the dimension associated with the device port to the dimension associated with the waveguide port.

19. The taper of claim 16, wherein the waveguide port is configured to couple to a two wire transmission line.

20. The taper of claim 16, further comprising:
    a substrate on which the tapered waveguide is defined; and
    a terahertz device formed at least partially in the substrate.

21. The taper of claim 20, further comprising at least one of:
    a cap layer situated on the substrate and configured to suppress terahertz wave coupling into the substrate,
    a thinned region of the substrate situated at the tapered waveguide; or
    the substrate is a one-dimensional photonic crystal.

22. A method, comprising:
    transmitting a terahertz electrical signal with a terahertz waveguide defined by at least one conductor; and
    coupling the terahertz electrical signal to a terahertz device with a conductive mode-matching taper situated between the terahertz waveguide and the terahertz device.

23. The method of claim 22, wherein the terahertz device is a terahertz generator.

24. The method of claim 22, wherein the terahertz device is a terahertz detector.

25. The method of claim 22, further comprising:
    directing the terahertz electrical signal from the terahertz waveguide to a specimen; and
    detecting the terahertz electrical signal after interaction with the specimen.

26. The method of claim 22, further comprising generating the terahertz electrical signal with a pulsed optical beam or based on a combination of two or more optical beams having a terahertz frequency difference.

* * * * *